(12) United States Patent
Prelewitz

(10) Patent No.: US 7,105,849 B2
(45) Date of Patent: Sep. 12, 2006

(54) HYDROCARBON FLUID ANALYSIS MODULE

(75) Inventor: David F. Prelewitz, Rochester, NY (US)

(73) Assignee: Technology Innovations, LLC, West Henrietta, NY (US)

(*) Notice: Subject to any disclaimer, the term of this patent is extended or adjusted under 35 U.S.C. 154(b) by 290 days.

(21) Appl. No.: 10/441,840

(22) Filed: May 20, 2003

(65) Prior Publication Data

US 2004/0232362 A1  Nov. 25, 2004

(51) Int. Cl.
  *G01N 15/06* (2006.01)
  *G01N 21/00* (2006.01)
(52) U.S. Cl. .................. 250/573; 250/574; 356/436
(58) Field of Classification Search ............. 356/436, 356/481, 73; 250/573, 574, 257; 48/84, 48/110; 67/79; 585/6; 204/228.3; 73/861
See application file for complete search history.

(56) References Cited

U.S. PATENT DOCUMENTS

| 5,305,071 | A | * | 4/1994 | Wyatt .......................... 356/73 |
| 5,637,881 | A | * | 6/1997 | Burghard et al. ........... 250/573 |
| 5,999,250 | A | * | 12/1999 | Hairston et al. .............. 356/73 |
| 6,023,340 | A | * | 2/2000 | Wu et al. .................... 356/432 |
| 6,153,873 | A | * | 11/2000 | Wolf ....................... 250/208.1 |
| 6,646,742 | B1 | * | 11/2003 | Gangstead et al. ......... 356/342 |
| 6,704,109 | B1 | * | 3/2004 | Wu et al. ................... 356/417 |

* cited by examiner

*Primary Examiner*—Georgia Epps
*Assistant Examiner*—Don Williams
(74) *Attorney, Agent, or Firm*—Thomas B. Ryan; Stephen B. Salai, Esq.; Harter, Secrest & Emery LLP

(57) ABSTRACT

Apparatus and method for quantifying the oil and water fractions of a multi-phase flow stream and their respective flow rates. The hydrocarbon fractions are determined based on information gathered on their respective refractive indices when exposed to particular wavelengths of light.

13 Claims, 12 Drawing Sheets

OPTICAL LAYOUT

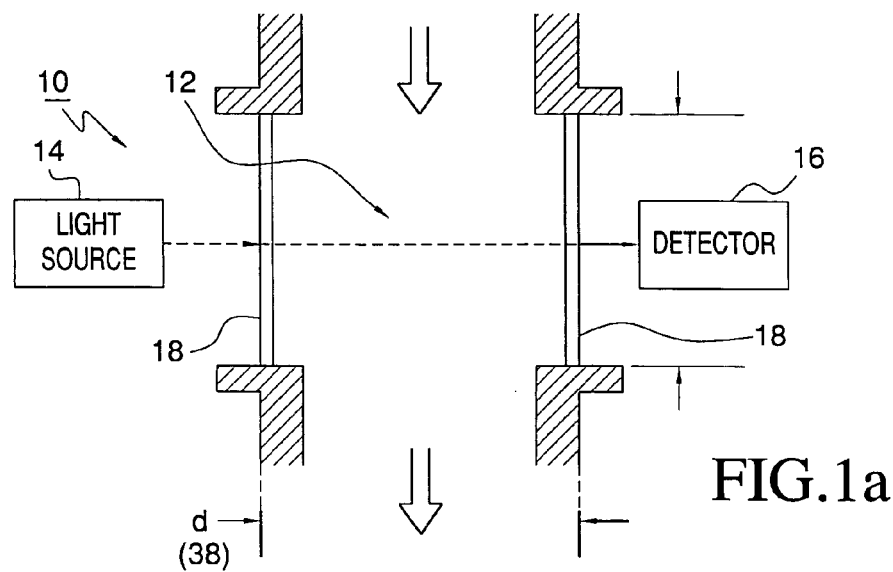
FIG.1a
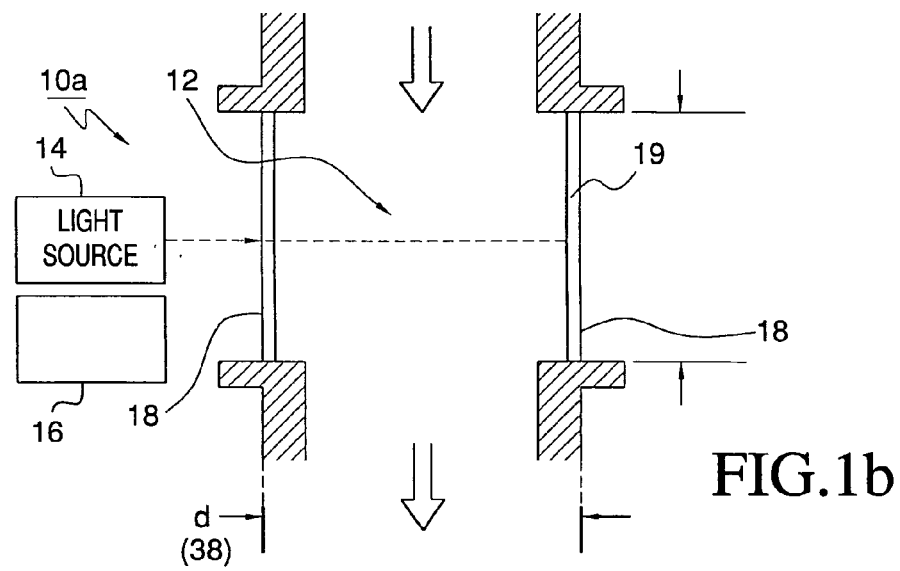
FIG.1b
FIG.7
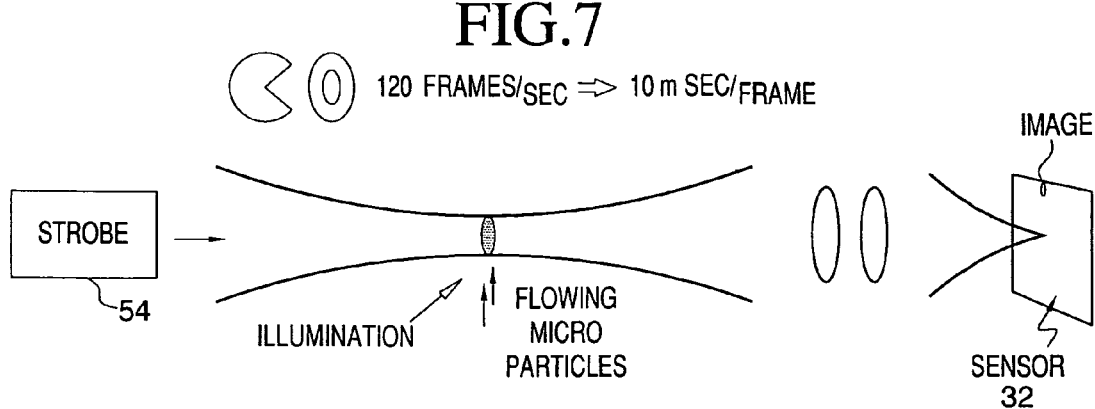

OPTICAL LAYOUT

SHACK-HARTMANN SENSOR

US 7,105,849 B2

HYDROCARBON FLUID ANALYSIS MODULE

BACKGROUND OF THE INVENTION

1. Field of the Invention

This invention relates to an apparatus and method for analyzing oil and water fractions in multi-phase fluid flow. This invention further and more particularly relates to determining the various hydrocarbon fractions in a fluid flow.

2. Background Art

In many situations the monitoring of a changing fluid flow in real time is desired in addition to determining the type of oil being produced without using a computer-intensive technique.

Also, it is necessary to analyze three-phase flow for the relative amounts of water, oil, and gas contained therein, and for distinguishing between the hydrocarbons and water.

It is desirable to make measurements without having to recalibrate each time a measurement is taken. Different material properties require recalibration of currently used equipment. This invention addresses this problem.

BRIEF SUMMARY OF THE INVENTION

This invention relates to an apparatus and method for analyzing oil and water fractions in multi-phase flow using the refractive index of hydrocarbon materials in relation to specific wavelengths of light. The method determines the percentages of hydrocarbon fractions, include passing a focused light beam through the hydrocarbon fluid flow, measuring the displacement of the point of focus from a known focal point with a known index of refraction, and thereby calculating the percentages of hydrocarbon fractions present.

BRIEF DESCRIPTION OF THE SEVERAL VIEWS OF THE DRAWING(S)

FIG. 1a is a diagram of the hydrocarbon fluid analysis module of this invention.

FIG. 1b is a diagram of another hydrocarbon fluid analysis module.

FIG. 7 shows a fluid stream that can be analyzed using this invention to determine the rate of flow.

DETAILED DESCRIPTION OF THE INVENTION

Figure 2:
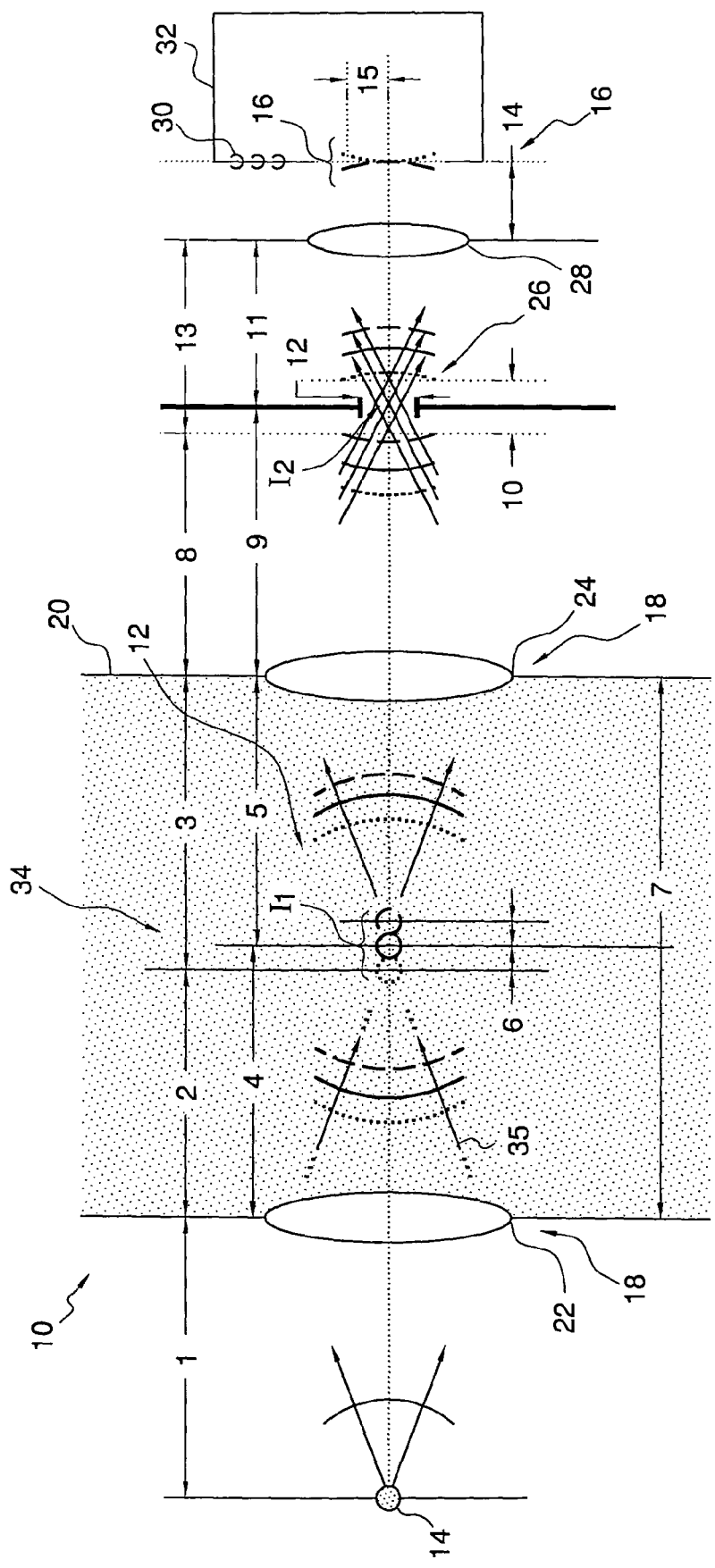
FIGS. 2 and 2a show a schematic of the hydrocarbon fluid analysis module.

Oil wells typically produce a fluid mixture of oils, water, and natural gas. A two-phase separator is used to remove the gas portion of the fluid, leaving an oil and water mixture. In contrast to the known detection systems that utilize absorption sensing devices, this invention measures wavefront distortions. This system can also be applied in a variety of other scenarios that will be discussed later.

Fluids, specifically those of different densities, refract light by varying degrees. The amount of refraction is a function of fluid composition and wavelength of the light passing through the fluid. A physical property of the fluid (hereafter referred to as "refractive index") is a parameter for determining the optical interaction of the fluid and the light refracted through it. As light is directed through the fluid sample, it will pass through the different hydrocarbon and water fractions. At each fraction boundary the incident light will be partly reflected and party refracted. Light is scattered by fraction boundaries, molecular excitations (Raman scattering) and by collective modes of the medium (e.g., Rayleigh scattering). In general, only a very small fraction of the light is scattered by the Raman and Rayleigh scattering processes. Rather, depending upon the fluid, much of the light is reflected and refracted. The refraction mechanisms of interest for the present invention result from the various hydrocarbon densities with respect to the different wavelengths of the refracting light. It is often also helpful to know the flow domain (i.e., laminar or slug) in advance, in addition to having a knowledge of the refractive indices of all but one hydrocarbon fraction.

FIG. 1a shows a hydrocarbon fluid analysis module 10 deployed to analyze a fluid mixture 12 of hydrocarbons and water, as well as other materials such as particulate matter, drilling mud, and materials that could be found in a hydrocarbon mixture, whether being produced from a well bore, during drilling, or in a laboratory for testing purposes. The hydrocarbon fluid analysis module 10 has a light source 14 and a detector 16 arranged on opposite sides of the flowing hydrocarbon fluid mixture 12. The hydrocarbon fluid analysis module 10 is such that there are transparent, or partially transparent, openings 18 between the light source 14 and the detector 16 that allow light to pass from the light source through the hydrocarbon fluid mixture 12 to the detector 16. The hydrocarbon fluid analysis module 10 can incorporate any number of optical elements, including but certainly not limited to lenses, filters, diffraction gratings, and other optical elements that will be discussed in detail later. These optical elements can be incorporated into the openings 18 or can stand alone.

The light source 14 is a point source or extended point source with one or more discrete wavelengths temporally and/or spatially separated such as would be true for a single source that is pulsed or one or more spatially separated sources. The source can include one or more discrete wavelengths or be a filtered white light source. If there are two or more light sources they can have overlapping spectra but two wavelengths must be at least detectable so that there is sufficient energy that is unique to each wavelength to provide two unique refractive properties after the light has passed through the fluid mixture. Note that alternatively a wideband white light source could be used unfiltered (without discrete wavelengths detectable at the source) and filtered at the detector. What is required is that the two wavelengths must be discrete to provide distinct and separate information when separately focused. Each discrete wavelength will be separately focused and the shift in the focal point measured from a known focal point.

FIG. 1b shows a hydrocarbon fluid analysis module 10a to analyze the fluid mixture 12 where the detector 16 is in an alternate location. The hydrocarbon fluid analysis module 10a has a second surface 19 that can incorporate the detector 16 or may be reflective or partially reflective such that the detection of a component may be directly read, recorded on the surface 19 or reflected toward another location. This embodiment could incorporate a circuit that diverted the focal point electronically as could the other embodiments.

Figure 2A:
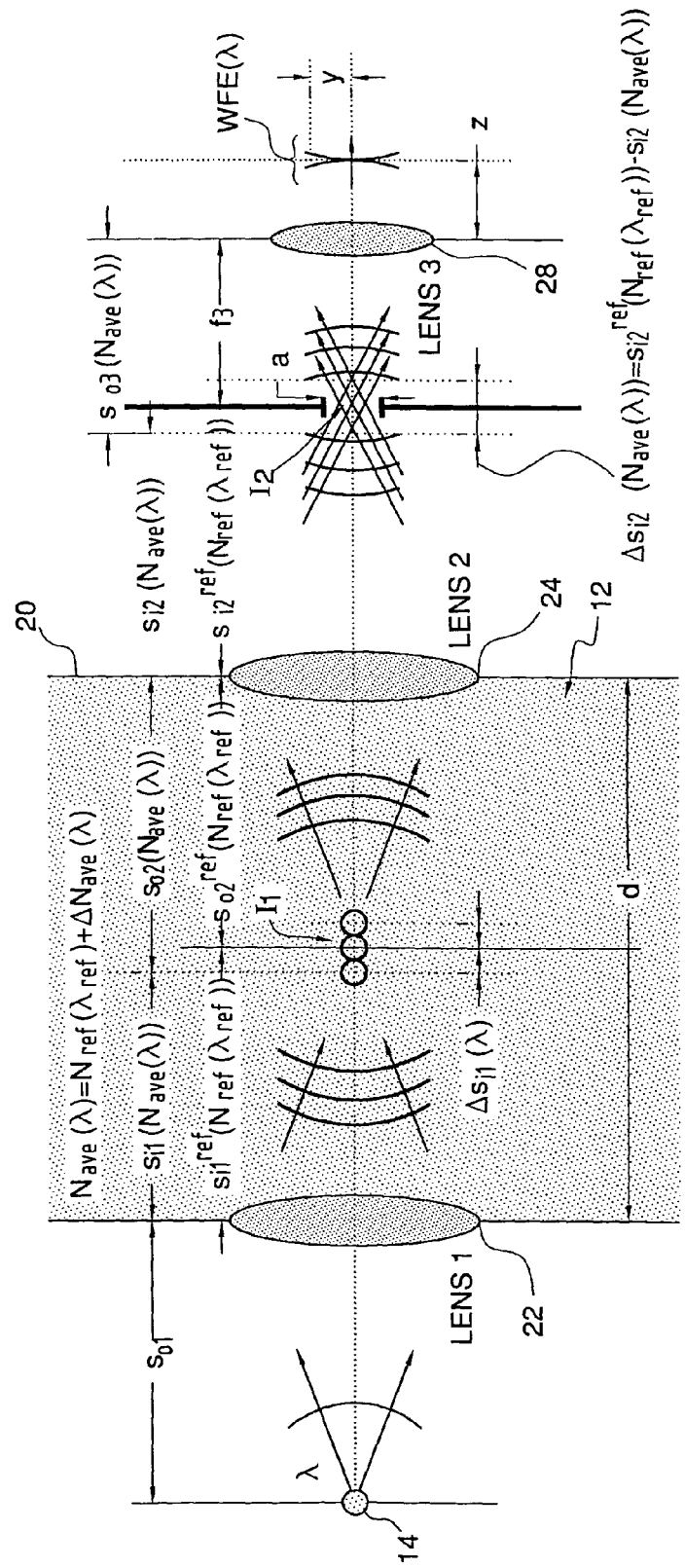

FIGS. 2 and 2a are a detailed schematic diagram of the hydrocarbon fluid analysis module 10 shown in a flow line 20 which could be the flow line of a producing oil well, in a drill string during drilling in a flow line during testing or even in a container in the field or in a laboratory. The fluid mixture 12 is shown between the light source 14 and the detector 16. In this embodiment there is a first quadradric phase plate ($L_1$) 22 and a second quadradric phase plate ($L_2$) 24 both of which preferably are positive lenses, and hereafter referred to as first lens 22 and second lens 24. Light from the source 14 can be focused in the fluid mixture 12 where a real image ($I_1$) of the source 14 is formed by $L_1$. The light travels on to $L_2$ which can form another image ($I_2$) near an aperture or spatial filter 26 before being focused by a third collimating lens 28 onto the lens array 30 and an area sensor 32 which could be a focal plane array. It is not necessary that the focus occur in the fluid mixture 12. The volume of the fluid mixture 12 that is being analyzed will be referred as the analysis zone 34 in the following discussion. The analysis zone is also referred to as a capturing cone. The fact that this covers a larger volume allows integration and averaging of a larger volume of fluid mixture 12.

Figure 3A:
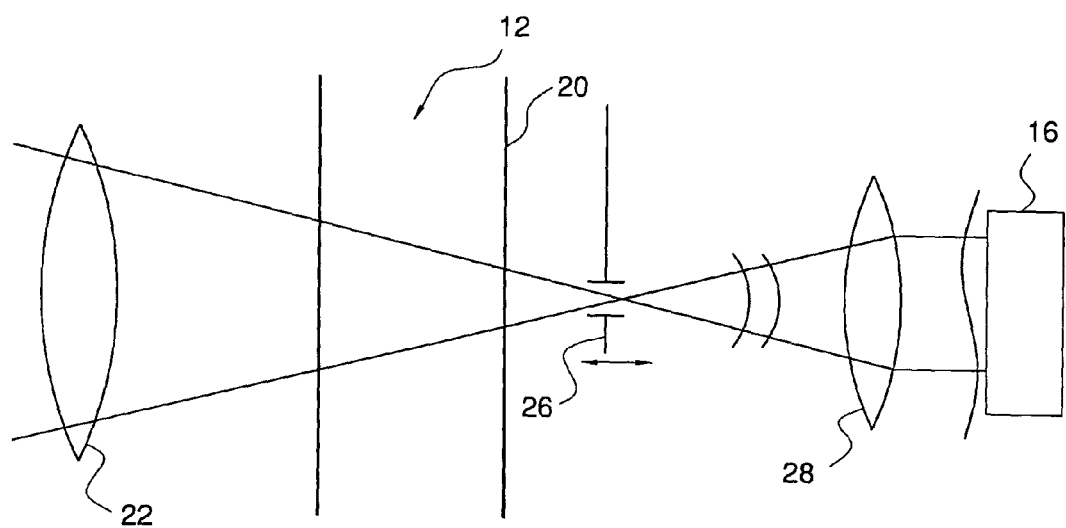
FIG. 3a–3c show schematic diagrams of the hydrocarbon fluid analysis module.
Figure 3B:
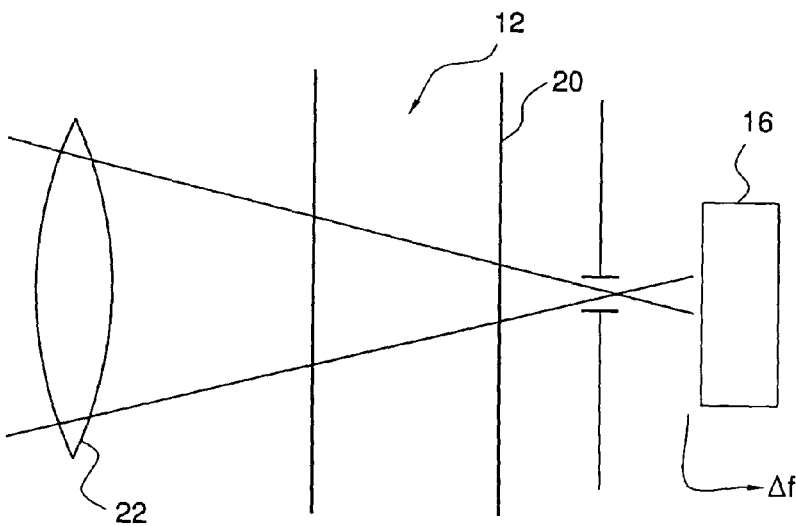
Figure 3C:
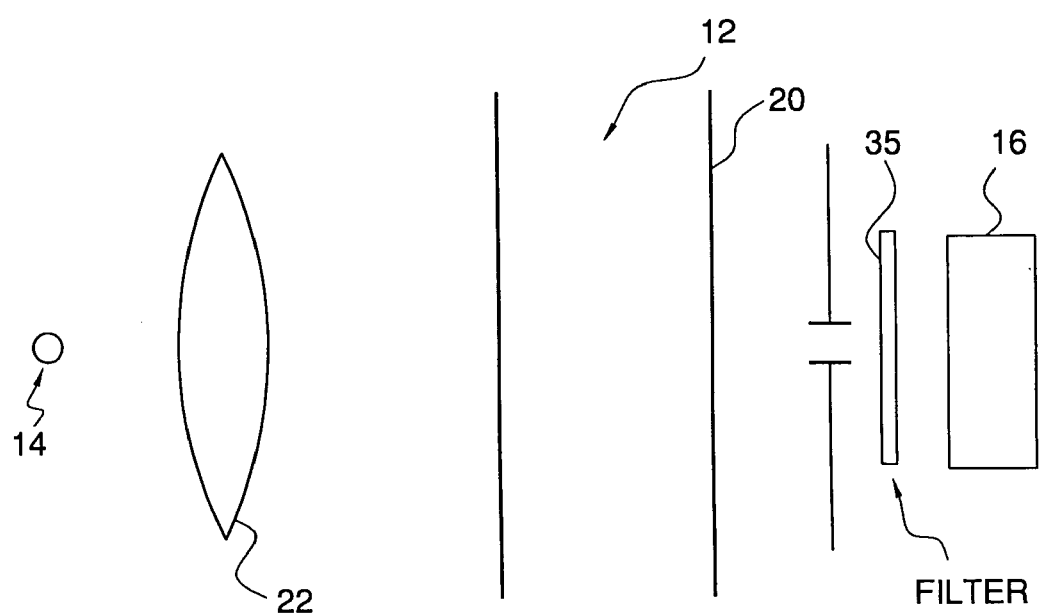

FIG. 3a; FIG. 3b, and FIG. 3c show alternate arrangements of the light source 14 and the detector 16 as well as one or more lenses that would work under certain circumstances. FIG. 3a has the first lens 22, the aperture 26, and the collimating lens 28. FIG. 3b does not have the collimating lens 28 and so the detector 16 must be able to handle light that has not been collimated. In this scenario, it may be more difficult to determine a unique solution due to the presence of higher order distortions. The same would be true if the collimating lens 28 was present but the aperture 26 was removed. The aperture 26 is not required in certain circumstances. FIG. 3c adds a filter 35 so that a white light source can be used without a filter at the source but with some sort of filter at the detector 16. The detector filter could even be an electronic device or involve an algorithm.

Figure 4:
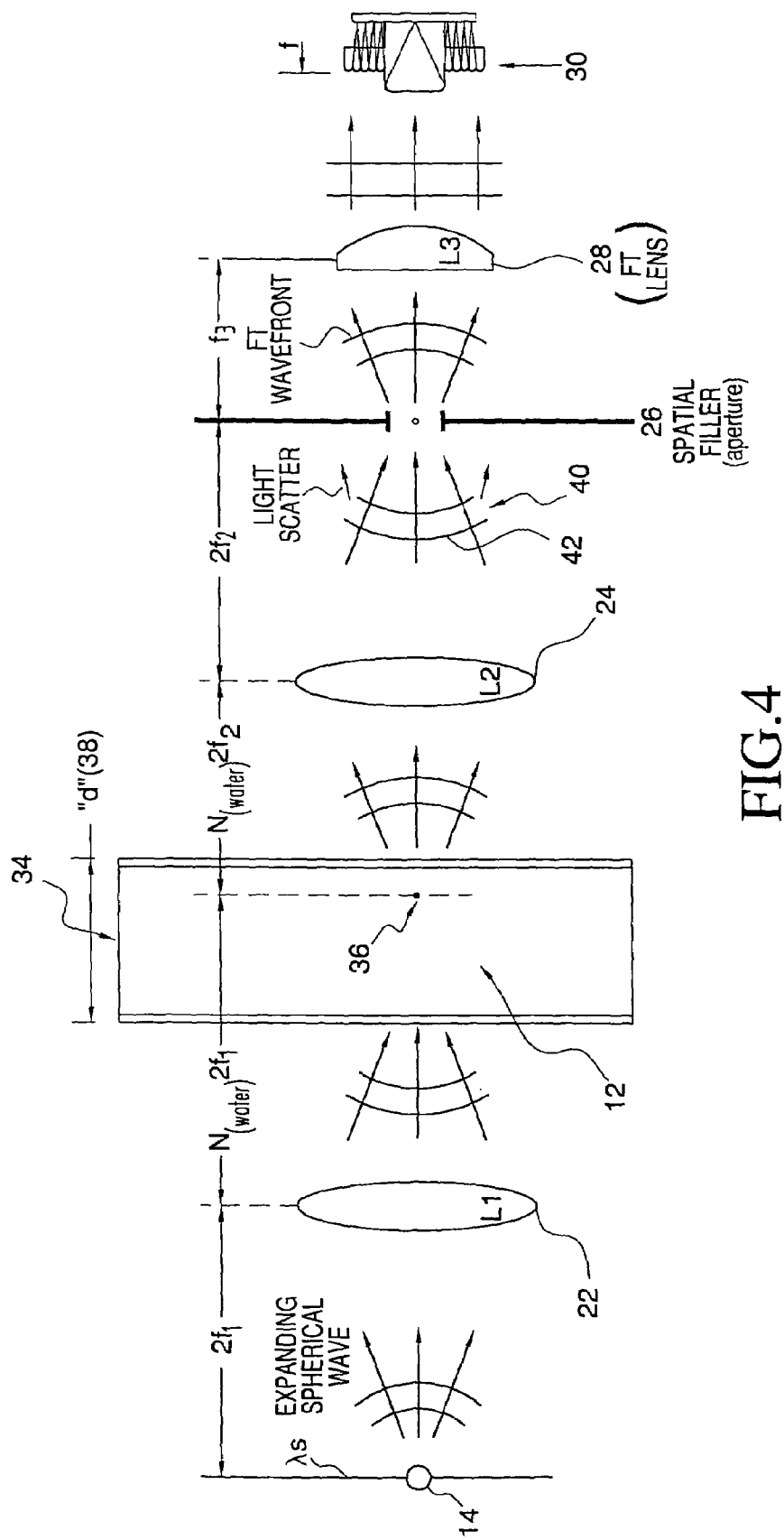
FIG. 4 is a schematic diagram of one embodiment of the hydrocarbon fluid analysis module with an area sensor and lens array.

FIG. 4 shows the light source 14 directed toward the first lens ($L_1$) 22 which in this case is shown to be at a distance that is twice its focal length from the light source. The first lens could be any distance from the light source as would be known in the art as long as the expanding wave front is known as it enters the fluid mixture 12. The wave front will be refracted by the first lens 22, refracted through the fluid mixture 12, and in this embodiment, if refracted through pure water, would focus at a point 36 between the first lens 22 and the second lens 24. The focal point 36, if the fluid mixture 12 was pure water, would-be $N_{water}$ (refractive index of water)·2·$f_1$ (focal length of the first lens 22) from the first lens 22, and a distance equal to $N_{water}$ (refractive index of water)·2·$f_2$ (focal length of the second lens 24) from the second lens 24. The lenses 22 and 24 are separated by a distance "d" shown by 38. The emerging light would be focused by the second lens 24 and directed toward the spatial filter 26, which in this embodiment is a distance equal to 2·$f_2$ from the second lens 24. After passing through the hydrocarbon fluid analysis module 10, the light wave front has been distorted by scattering in the fluid. The distorted wave front, represented by 40 in the diagram, would defocus by higher order terms incorporated in it, as shown in the diagram by the wavy line 42. After this distorted wave front 40 passes through the spatial filter or aperture 26, the wave front has some of the noise eliminated. The choice of an aperture or spatial filter 26 is important to the success of this apparatus because, like a confocal microscope, it eliminates noise (higher order distortions) without removing the focus information. If the aperture is too small the information that includes the mixture dependent focus would be lost. If the aperture is too large, unnecessary noise would detract from the efficiency of the apparatus. All of the distances must be measured precisely since the shift in the focal point will be the order of a wavelength.

The filter aperture requirements (size, geometry, etc.) are heavily dependent on the optical system layout and the defined measurement tolerances. Given that defocus shifts are the primary wavefront aberration to be measured, all other contributions to the WFE (wavefront error) can be ignored. The filter aperture 26 can help reduce the other aberrations (typically, of a higher order than defocus), which are primarily due to scattering generated by the material being measured. A basic review of how to deal with such things can be found in Goodman's book "Introduction to Fourier Optics", in chapter and section: "Frequency analysis of optical imaging systems, Aberrations and their effects on frequency response" (Chapter 6–4 in the $1^{st}$ edition). Here, the generalized exit pupil function is defined as:

$$P(x_p, y_p) = p(x_p, y_p)\exp(jkW(x_p, y_p)), \text{ where } p(x_p, y_p)$$

is the non-aberrated pupil function applied to the image at aperture 26. $W(x_p, y_p)$ encompasses the aberration phase terms of the exit pupil wavefront. Assuming defocus is the dominant term we have:

$$W(x_p, y_p) = \frac{\varepsilon(x_p^2 + y_p^2)}{2} + \text{Higher order terms,}$$

where $\varepsilon$ is the phase error term. The specified shifts in defocus are related to $\varepsilon$ and an aperture 26 can be constructed such that the higher order contributions are minimized with respect to the desired measurable defocus range.

In this embodiment the third collimating lens 28 (also referred to as "a fourier transform lens" or "FT lens") is placed a distance equal to its focal length from the spatial filter 26. The third, collimating lens 28 essentially turns the wavefront "inside out" and the focus information is the largest component of the light wavefront leaving the collimating lens 28. The light is focused on the lens array 30 of this embodiment which could take many different formats (such as Shack-Hartmann, Interferometry phase diversity, various algorithms, electric circuits, etc.). A Shack-Hartmann area sensor 32 can perform an inverse fourier transform resulting in spot shifts when a refractive index of the fluid mixture 12 changes. If the parameters are carefully chosen there is no shift when the medium is water, there is a positive shift when there is oil present, and there is a negative shift when there is gas present allowing a simple deflection measurement to determine the fraction of oil or gas in a sample. The area sensor 32 could take another format, such as interferometer, which would require the transmission of an undistorted wave front from the light source 14 to the detector 16 to the area sensor 32 in order to get the interference necessary for the interferometer to work. In which case, there would be no need for the collimating lens 28.

Figure 5A:
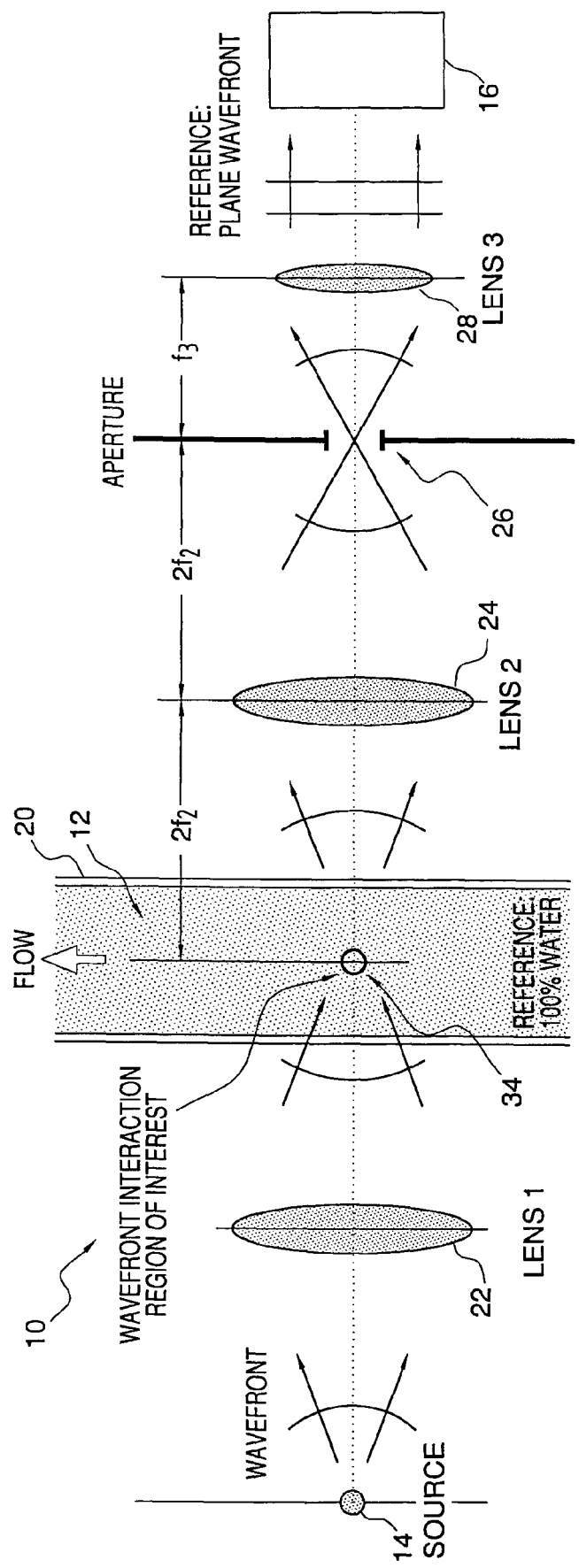
FIG. 5a is a schematic diagram of the hydrocarbon fluid analysis module with a reference fluid.

FIG. 5a is a schematic diagram of the hydrocarbon fluid analysis module 10 and a reference fluid with a known refractive index such as water, calibrated so that the focus of the light passed through at the detector 16.

Figure 5B:
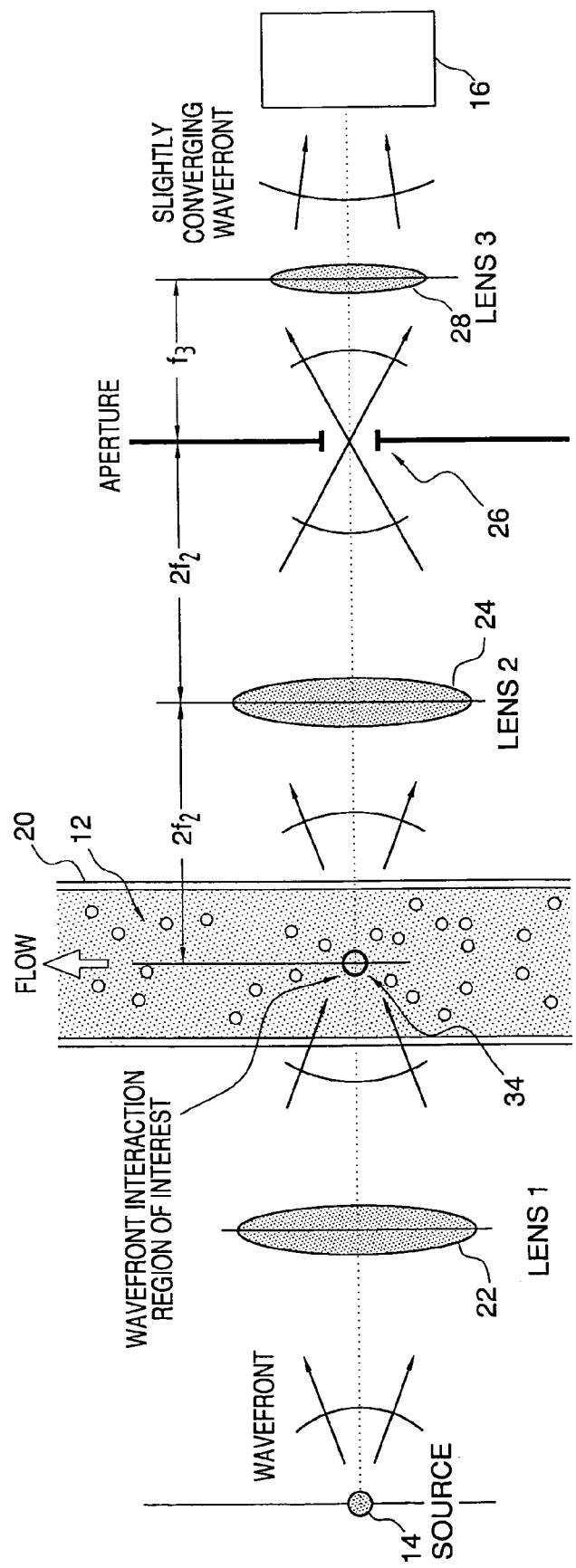
FIG. 5b is a schematic drawing of the hydrocarbon fluid analysis module with the reference material and another lighter fluid.

FIG. 5b is a schematic drawing of the hydrocarbon fluid analysis module 10 and both the reference fluid and another lighter fluid such that the focal point changes in relation to the change in refractive index due to the amount of hydrocarbon in the mixture.

Figure 5C:
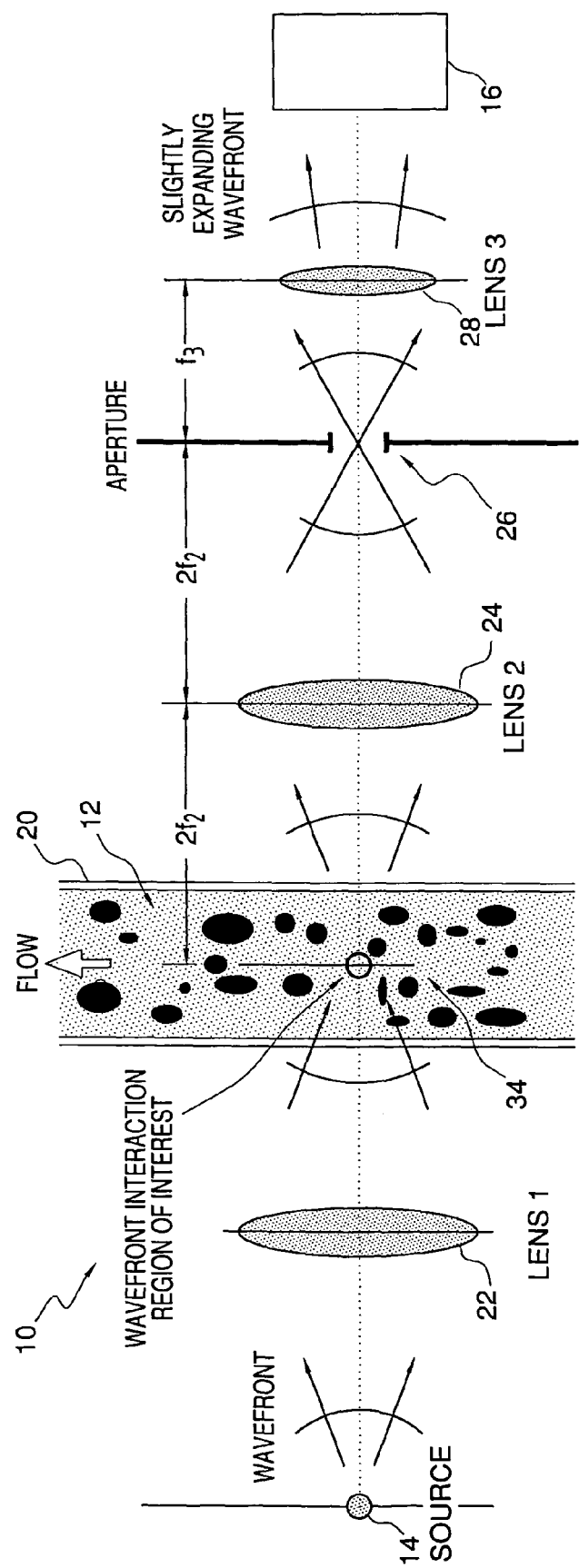
FIG. 5c is a schematic drawing of the hydrocarbon fluid analysis module with the reference material and another heavier fluid.

FIG. 5c is a schematic drawing of the hydrocarbon fluid analysis module 10 and both the reference fluid and another heavier fluid such that the focal point changes in relation to the change in refraction index due to the heavier fluid. Note that the focal point will shift in a direction opposite of that in FIG. 4b in this example. The introduction of the lighter gas causes less refraction because the light is traveling through a fluid with a lower refractive index.

Figure 5D:
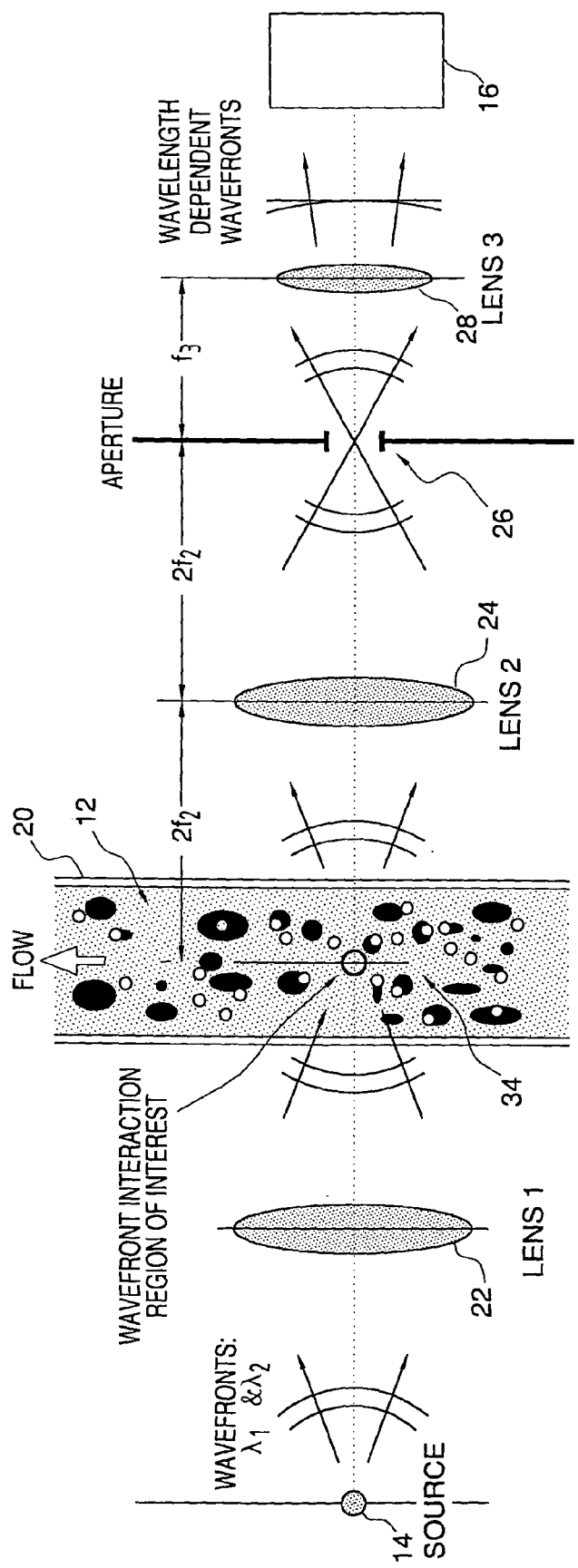
FIG. 5d is a schematic drawing of the hydrocarbon fluid analysis module with the reference material and with both a lighter and a heavier fluid.

FIG. 5d is a schematic drawing of the hydrocarbon fluid analysis module 10 and the reference fluid, as well as both a lighter and a heavier fluid so that there is the need to focus two different wavelengths of light to solve for the two unknown fractions of hydrocarbons present.

Figure 5E:
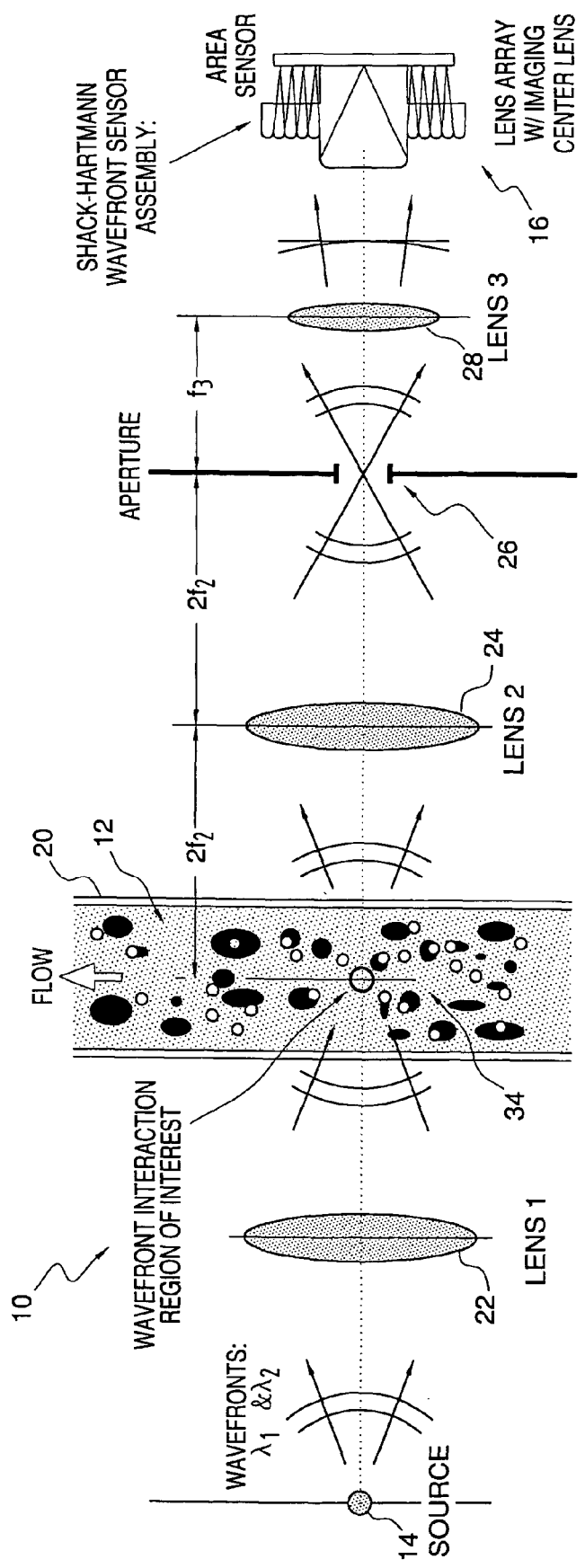
FIG. 5e is a schematic drawing of the hydrocarbon fluid analysis module and a Shack-Hartmann detector.

FIG. 5e is a schematic drawing of the hydrocarbon fluid analysis module 10 with all three phases of fluid and a Shack-Hartmann detector.

This invention is particularly applicable to production logging, production facilities, drill string testing or any flow stream or volume that contains hydrocarbons and other materials like water and drilling mud. It is not necessary to know the refractive index of the hydrocarbon fractions in order to use this method. The hydrocarbon fluid analysis module 10 can be connected to a flow line such that the hydrocarbon fluids to be analyzed pass through it. It should be appreciated, however, that it is not intended that the invention be limited to any particular method or apparatus for obtaining the hydrocarbon fluids. It is noted, however, that preferably, the hydrocarbon fluid analysis module 10 which is used to practice the preferred method of the invention may include a processor (not shown) for carrying out calculations as set forth below.

Figure 6:
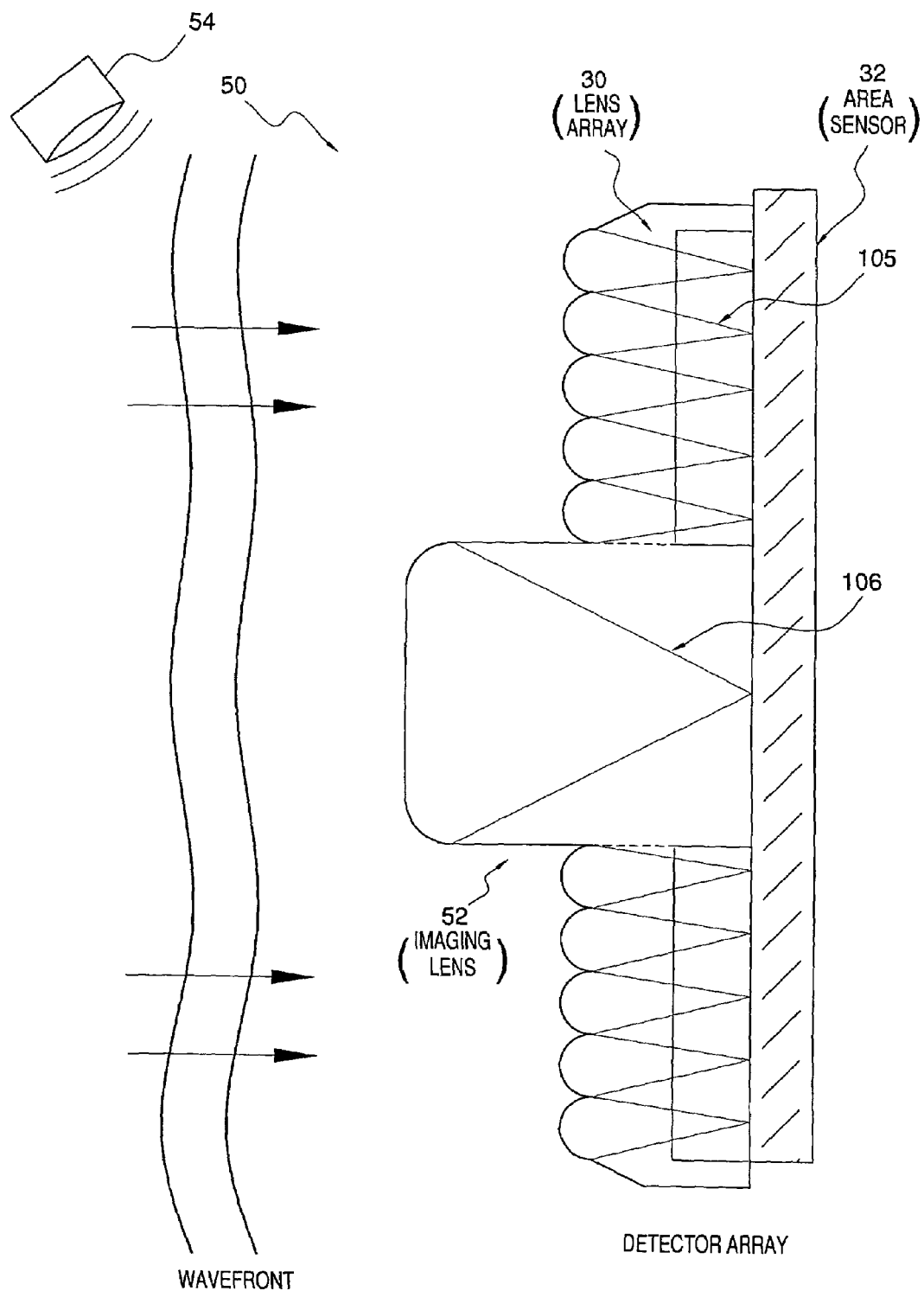
FIG. 6 is an embodiment with an imaging lens.

The hydrocarbon fluid analysis module 10 is set to analyze a fluid flow of a hydrocarbon mixture as shown in FIG. 6. This fluid flow could be part of a pipeline, flow line, or it could be in a drill stream for drill stem testing, or in a separate vessel or system in a laboratory. The hydrocarbon fluid analysis module 10 can be used to analyze hydrocarbon and water fractions in a flow. While the light source is shown to produce two or more discrete wavelengths, it will be appreciated that any light source producing a plurality of distinct wavelengths could be utilized, if the wavelengths can be separately focused. If there is only one unknown fraction then one known wavelength and one measurement of displacement from a known focal point is sufficient to determine the unknown fraction.

FIG. 7 shows a fluid stream that can be analyzed using this invention to determine the rate of flow.

One embodiment of the method for measuring the hydrocarbon fractions includes projecting two discrete wavelengths, $\lambda_1$ and $\lambda_2$, through the flowing hydrocarbon fluid mixture 12 causing wave front distortions allowing for the determination of two separate focal point displacements and the determination of two hydrocarbon fractions in response to the measurements generated by $\lambda_1$ and $\lambda_2$. This method requires values of $\lambda_1$ and $\lambda_2$ such that:
(a) $\lambda_1$: chosen such that $N_{oil}(\lambda_1) \neq N_{water}(\lambda_1)$; $N_{oil}(\lambda_1) \neq N_{gas}(\lambda_1)$; and
(b) $\lambda_2$: chosen such that $N_{oil}(\lambda_2) \neq N_{water}(\lambda_2)$; $N_{oil}(\lambda_2) \neq N_{gas}(\lambda_2)$.

In order to solve for the fractions of oil, gas, and water, the following equation is solved where:
(a) OPL=Optical Path Length (measured by the refractometer)
  (i) OPL[measured]=$N_{avg}(\lambda)t$.
  (ii) $AN_{oil}(\lambda_1)+BN_{water}(\lambda_1)+CN_{gas}(\lambda_1)=N_{avg}(\lambda_1)$
  (iii) $AN_{oil}(\lambda_2)+BN_{water}(\lambda_2)+CN_{gas}(\lambda_2)=N_{avg}(\lambda_2)$
  (iv) A+B+C=1
  (v) $N(\lambda)$=refractive index and is known for water and gas but unknown for oil. A, B, C are coefficients for oil, gas and water respectively.

First the first $\lambda_1$ is focused and the distance from the known focus in water measured so that $N_{avg}(\lambda_1)$ can be calculated. Subsequently, the second $\lambda_2$ is focused, the distance from the known focus measured, and $N_{avg}(\lambda_2)$ calculated. With all but A, B, and C known the coefficients A, B, and C can be calculated from the three equations.

If the refractive index of oil ($N_{oil}$) is also unknown, then there are four unknowns (A, B, C and $N_{oil}$) since only $N_{water}$ and $N_{gas}$ are known. To solve these equations, four wavelengths ($\lambda_1$, $\lambda_2$; $\lambda_3$, $\lambda_4$) must be focused and the distance from a known focal point measured for each [$N_{avg}(\lambda_1)$; $N_{avg}(\lambda_2)$, $N_{avg}(\lambda_3)$, $N_{avg}(\lambda_4)$]. The $N_{oil}$ varies in a known way according to the Cauchy relationship such that:
$N(\lambda_1) \propto K_1 + K_2 N(\lambda_1^2)$, where the higher order terms are ignored, and then $N_{oil}$, A, B, and C can be solved for simultaneously. Including additional terms in the Cauchy expansion will require additional wavelengths in order to find a solution.

A detailed analysis using the physical arrangement shown in FIG. 2 follows:
a) Dimension Items
  (i) $s_{o1}$—Distance of light source (14) to the $1^{st}$ principle plane of Lens 1 (22)
  (ii) $s_{i1}(N_{ave}(\lambda))$—Distance of imaged light source ($I_1$) to the $2^{nd}$ principle plane of Lens 1 (22) for $N_{ave}(\lambda)$
  (iii) $s_{o2}(N_{ave}(\lambda))$—Distance of imaged light source ($I_1$) to $1^{st}$ principle plane of Lens 2 (24) for $N_{ave}(\lambda)$
  (iv) $s_{i1ref}(N_{ref}(\lambda_{ref}))$—Reference distance of imaged light source ($I_1$) to $2^{nd}$ principle plane of Lens 1 (22) for $N_{ref}(\lambda_{ref})$
  (v) $s_{o2ref}(N_{ref}(\lambda_{ref}))$—Reference distance of imaged light source ($I_1$) to $1^{st}$ principle plane of Lens 2 (24) for $N_{ref}(\lambda_{ref})$
  (vi) $\Delta s_{i1}(\lambda)$—Change in $s_{i1}$ relative to reference at $S_{i2ref}$ due to wavelength and material changes between Lens 1 (22) and Lens 2 (24)
  (vii) d—Thickness of the material to be analyzed
  (viii) $s_{i2}(N_{ave}(\lambda))$—Distance of imaged light source ($I_2$) to the $2^{nd}$ principle plane of Lens 2 (24) for $N_{ave}(\lambda)$
  (ix) $s_{i2ref}(N_{ref}(\lambda_{ref}))$—Reference distance of imaged light source ($I_2$) to $2^{nd}$ principle plane of Lens 2 (24) for $N_{ref}(\lambda_{ref})$
  (x) $\Delta s_{i2}(N_{ave}(\lambda))$—Change in $s_{i2}$ relative to reference at $s_{i2ref}$ due to wavelength and material changes between Lens 1 (22) and Lens 2 (24)
  (xi) $f_3$—Effective focal length of Lens 3 (28)
  (xii) $\alpha$—Aperture size
  (xiii) $s_{o3}(N_{ave}(\lambda))$—Distance of imaged light source ($I_2$) to $1^{st}$ principle plane of Lens 3 (28) for $N_{ave}(\lambda)$ (xiv) z—Distance from aperture 26 to where the WFE (wavefront error) is measured (xv) y—Distance perpendicular from optical center line to where the WFE is measured (xvi) WFE($\lambda$)—Paraxial Wavefront Error (measured in waves of $\lambda_{ref}$) relative to reference due to wavelength and material changes between Lens 1 (22) and Lens 2 (24)

b) Glossary:
(i) $\lambda \equiv$ Wavelength
(ii) $\lambda_{ref} \equiv$ Reference wavelength
(iii) N$\equiv$Refractive index
(iv) f$\equiv$Effective focal length for all $\lambda$ to be used in device, where f>0 for all lenses
(v) $N_{ref}(\lambda_{ref}) \equiv$ Index of a reference component (m=0) at a reference wavelength ($\lambda_{ref}$)
(vi) $A_m \equiv$ Solution component volume percentage
(vii) n$\equiv$Number of solution components c) Known Terms:
(i) $\lambda_{ref}$, $N_{ref}(\lambda_{ref})$, $f_1$, $f_2$, $f_3$, $s_{o1}$, and d d) Equations:

$$N_{ave}(\lambda) = N_{ref}(\lambda_{ref}) + \Delta N_{ave}(\lambda) = \sum_{0}^{n-1} A_m N_m(\lambda) \quad \text{(i)}$$

$$s_{refi2}(\lambda) = \frac{df_2 - N_{ref}(\lambda_{ref})f_1 f_2 s_{ol}/(s_{ol} - f_1)}{d - N_{ref}(\lambda_{ref})[f_2 - f_1 s_{ol}/(s_{ol} - f_1)]} \quad \text{(ii)}$$

$$s_{i2}(\lambda) = \frac{df_2 - N_{ave}(\lambda)f_1 f_2 s_{ol}/(s_{ol} - f_1)}{d - N_{ave}(\lambda)[f_2 - f_1 s_{ol}/(s_{ol} - f_1)]} \quad \text{(iii)}$$

$$\Delta s_{i2}(\lambda) = s_{refi2}(\lambda) - s_{i2}(\lambda) = \frac{df_2 - N_{ref}(\lambda_{ref})f_1 f_2 s_{ol}/(s_{ol} - f_1)}{d - N_{ref}(\lambda_{ref})[f_2 - f_1 s_{ol}/(s_{ol} - f_1)]} - \frac{df_2 - N_{ave}(\lambda)f_1 f_2 s_{ol}/(s_{ol} - f_1)}{d - N_{ave}(\lambda)[f_2 - f_1 s_{ol}/(s_{ol} - f_1)]} \quad \text{(iv)}$$

$$s_{o3}(\lambda) = f_3 - \Delta s_{i2}(\lambda) \quad \text{(v)}$$

$$s_{i3}(\lambda) = \frac{s_{o3} f_3}{s_{o3} - f_3} = f_3 - \frac{f_3^2}{\Delta s_{i2}(\lambda)} \quad \text{(vi)}$$

$$WFE(\lambda) = \frac{|s_{i3}(\lambda) - z| - \sqrt{(s_{i3}(\lambda) - z)^2 - y^2}}{\lambda_{ref}} \quad \text{(vii)}$$

$$= \frac{1}{\lambda_{ref}}\left[\left|f_3 - \frac{f_3^2 11}{\Delta s_{i2}(\lambda)} - z\right| - \sqrt{\left(f_3 - \frac{f_3^2}{\Delta s_{i2}(\lambda)} - z\right)^2 - y^2}\right]$$

e) Number Run:
(i) $s_{o1}$=100 mm
(ii) $\lambda_{ref}$=1.4 µm
(iii) d=260 mm
(iv) y=10 mm
(v) z=50 mm
(vi) $f_1=f_2=f_3$=50 mm
(vii) $N_0(\lambda_{ref})$=1.3
(viii) $N_{ave}(\lambda)$=1.302
(ix) $\Delta s_{i2}(N_{ave}(\lambda))$=0.03691172 mm; $\therefore$
  WFE($\lambda$)$\approx$0.53 Waves @ $\lambda_{ref}$ Most wavefront sensors can easily measure errors to less than 1 wave, and given a small change of index, there is typically a significant change in the wavefront error produced. For the above case, where there is a 0.002 index change, the WFE is easily measurable.

Other properties that can be calculated include any physical property that has a relationship that changes with the refractive index. The refractive index relates to the interaction of light with the electrons in a substance, the more electrons, and the more polarizable the electrons, the higher the refractive index. Although viscosity is resistant to the shearing force, it is related to the interactions between molecules as they move past one another. It is possible to relate viscosity and other properties to the refractive index of light within a specific class of components, specifically hydrocarbons for example, by correlating the two properties and using the relationship. For example, for complex hydrocarbons, the viscosity increases because there is more opportunity for them to interact as they are moving past each other, and the refractive index also increases slightly because the density of electrons is a little higher. For this very restricted class, a correlation can be made that is valid for that class of hydrocarbons. Similar correlations could be made for other hydrocarbons.

In order for these equations to be solved, it is necessary that the fluid components do not chemically interact, such that the hydrocarbon fractions may be separated with the component ratios preserved. For example, when pure water is a reference fluid, the focal point changes as a function of the material in the flow stream. The light beam will curve (spread) when compared to the reference fluid. This curvature can be measured. There are a number of combinations that can be solved including a hydrocarbon phase refractive index or a ratio of hydrocarbon fractions. If there are two or more unknowns then additional wavelengths will be required to solve for the unknown.

The Shack-Hartmann Wavefront Analyzer is constructed by placing an array of apertures in front of a charge-coupled device or CCD camera. These apertures allow light be diffracted by the plate onto the CCD. The segments of the beam that pass through the apertures will be spatially displaced from the center position, based on the direction of travel, or the phase of that part of the beam. The CCD camera measures the phase of each spot by measuring this displacement. Software algorithms then reconstruct a wavefront for the entire beam. The spacing of the apertures defines the resolution of the system, and the size of each aperture is calculated to optimize sensitivity to phase changes. In contrast, a Shack-Hartmann Wavefront Analyzer uses an array of small lenslets to collect all of the beam in each aperture position, and project all of it onto a detector.

Essentially, a spherical wavefront is refracted through the fluid mixture 12, which will eventually be focused. It is preferred that the focus be located within the fluid mixture 12. A key component is the aperture or spatial filter 26 which eliminates the majority of the (waste) scattered light outside of the focus region. The aperture or spatial filter 26 functions as a noise filter. This is how confocal microscopy works. Additionally, the aperture size is optimized to account for focus shifts (+ or −) due to average volume index changes. Any wavefront can be propagated through the test region, if the wavefront is pre-determined before being transmitted through the distortion zone (e.g., an oil-water mix), and if there is a reference volume of fluid (e.g., water) to make a comparison with. An distortion dependent shift in focus (defocus) is going to be the largest distortion component, hence, the easiest to detect and measure (even in a noisy environment).

Concerning a flow rate method, a strobe will be used as shown in FIG. 7 and accommodations made for the fluid velocity profile in a pipe. The flow profile can be compensated by taking the flow rate at the center of the stream and at the edges and averaging, or testing at the center. LED's are strobed at different duty cycles until particles appear stationary (within a certain tolerance). Hence, the velocity of the fluid can be determined. The sensing array can have a central imaging lens to detect the flow rate and wavefront sensor lenslets to detect the wave front information and distortions. With a fixed imaging optic, the device measures the velocity of particulate matter in the focus region in the fluid using a strobe. If the fluid ratios and oil viscosity values are known, the volume fluid flow rate can be calculated if the center flow rate has been determined. By varying the gate time of the strobe, imaged particles may appear stationary once the gate time is correct.

With a fixed imaging optic, the device measures velocity of particulate matter in the focus region in the fluid using a strobe. With knowledge of the fluid ratios, and density values, the fluid volume flow can be determined. It is also possible to scan the imaging optic (using a speaker coil mounted optic as used in CD players) and collect a range of flow data.

A number of basic improvements result, which include:
a) reduction of errors due to optical scattering losses;
b) simplification of instrument calibration;
c) improved accuracy for low-water-cut (higher ratio of oil to water).
d) elimination of calibration step;
e) accurate measurements with 20% gas void fraction;
f) accurate multi-phase (oil/water/gas) detection system over all ratios; and
g) three-phase linear velocity measurement.

While the invention has been described in connection with a presently preferred embodiment thereof, those skilled in the art will recognize that many modifications and changes can be made therein without departing from the true spirit and scope of the invention, which accordingly is intended to be defined solely by the appended claims.

The invention claimed is:

1. A method of determining the amounts of first and second hydrocarbons having known, different indices of refraction in a hydrocarbon fluid mixture comprising:
    a) passing a focused light beam through the hydrocarbon fluid mixture;
    b) measuring the displacement of the actual point of focus in the hydrocarbon fluid mixture from a reference focal point through a reference material with a known index of refraction; and
    c) calculating the amounts of the first and second hydrocarbon present from the displacement.

2. The method of determining the amounts of hydrocarbons present in the hydrocarbon mixture as set forth in claim 1, comprising:
    a) passing a focused light beam having at least two discrete wavelengths through the hydrocarbon fluid mixture; and
    b) separately measuring the displacement of the actual point of focus from a reference focal point for each of said at least two discrete wavelengths.

3. The method of determining the amounts of hydrocarbons present as set forth in claim 1, comprising:
    filtering the emergent light beam to remove higher order distortions.

4. The method of determining the amounts of hydrocarbons present as set forth in claim 1, comprising:
    collimating the beam after it passes through the hydrocarbon mixture and before measuring the displacement of the focal point.

5. The method of determining the amounts of hydrocarbons as set forth in claim 4, in which measuring the displacement comprises measuring the shape of a collimated wavefront beyond the point of focus.

6. A method for measuring a flowing hydrocarbon fluid mixture having a plurality of fluid phases having different inches of refraction comprising:
    (a) projecting light of wavelength $\lambda_1$ through the flowing hydrocarbon fluid mixture to distort a wavefront of wavelength $\lambda_1$ relative to a reference wavefront;
    (b) projecting light of wavelength $\lambda_2$ through the flowing hydrocarbon fluid mixture to distort a wavefront of wavelength $\lambda_2$ relative to a reference wavefront;
    (c) determining phase information of the flowing mixture in response to the distortion of the light of wavelengths $\lambda_1$ and $\lambda_2$.

7. The claim of claim 6, wherein the phase information determines the refractive index of a hydrocarbon.

8. The claim of claim 6, wherein the phase information determines the ratio of hydrocarbon components.

9. The claim of claim 6, wherein the phase information determines both the refractive index and the ratio of hydrocarbon components.

10. A method of analyzing a flowing hydrocarbon fluid mixture with a plurality of fluid phases comprising:
    a) projecting light comprising $\lambda_1$ and $\lambda_2$ through the flowing hydrocarbon fluid mixture such that
       (i) $\lambda_1$: chosen such that $N_{oil}(\lambda_1) > N_{water}(\lambda_1) \approx N_{gas}(\lambda_1)$
       (ii) $\lambda_2$: chosen such that $N_{water}(\lambda_2) > N_{gas}(\lambda_2)$, $N_{water}(\lambda_2) \neq N_{oil}(\lambda_2)$;
    b) projecting the light set forth in step a) through the flowing hydrocarbon fluid mixture such that the focus indicates the hydrocarbon ratio is approximately 1.0 in water as a reference plane wave;
    c) further projecting light through an aperture and collimating lens array to an area sensor; and
    d) detecting the wavefront distortions relative to the reference wavefront described in step b) to determine hydrocarbon fractions.

11. The claim of claim 10, further comprising using a strobe to determine rate of the hydrocarbon fluid mixture.

12. An hydrocarbon refractometer for measuring the hydrocarbon fluid fractions in a flowing fluid mixture comprising:
    a) light source comprising wavelengths $\lambda_1$ and $\lambda_2$ such that when multiplied by the refractive index of each hydrocarbon fluid fraction, produces a distinct signature; and
    b) detection to sense the signature.

13. The claim of claim 12, further comprising using a Shack-Hartmann Wavefront Analyzer.

* * * * *